US 6,743,015 B2
Jun. 1, 2004

(12) United States Patent
Magnani

(10) Patent No.: US 6,743,015 B2
(45) Date of Patent: Jun. 1, 2004

(54) IONTOPHORETIC APPARATUS

(76) Inventor: Thomas J. Magnani, 382 North St., Greenwich, CT (US) 06830

( * ) Notice: Subject to any disclaimer, the term of this patent is extended or adjusted under 35 U.S.C. 154(b) by 0 days.

(21) Appl. No.: 10/123,938

(22) Filed: Apr. 15, 2002

(65) Prior Publication Data

US 2002/0132208 A1 Sep. 19, 2002

Related U.S. Application Data

(63) Continuation of application No. 09/658,841, filed on Sep. 8, 2000, now abandoned.

(51) Int. Cl.$^7$ .............................................. A61C 17/00
(52) U.S. Cl. ......................................... 433/80; 604/20
(58) Field of Search .......................... 433/80, 89, 215, 433/216, 32; 132/311; 604/20; 15/167.1

(56) References Cited

U.S. PATENT DOCUMENTS

| | | | | |
|---|---|---|---|---|
| 3,163,166 A | * | 12/1964 | Brant et al. ............... | 604/20 |
| 3,645,260 A | * | 2/1972 | Cinotti et al. ............. | 604/20 |
| 3,716,054 A | * | 2/1973 | Porter et al. .............. | 604/20 |
| 3,831,598 A | * | 8/1974 | Tice ....................... | 604/20 |
| 4,691,718 A | * | 9/1987 | Sakuma et al. ............ | 433/32 |
| 4,969,868 A | * | 11/1990 | Wang ...................... | 604/20 |
| 5,503,553 A | * | 4/1996 | Hines ..................... | 433/80 |
| 5,885,711 A | * | 3/1999 | Clarisse et al. ........... | 428/407 |

OTHER PUBLICATIONS

Collins, Edwin M., D.D.S., "Desensitization of Hypersensitive Teeth," *Dental Digest*, vol. 68, No. 7 at 360–363 (Jul., 1962).
Scott, Harold M. Jr., D.D.S., "Reduction of Sensitivity by Electrophoresis," *Journal of Dentistry for Children*, vol. XXIX, No. 4 at 225–241 (Fourth Quarter, 1962).

Jensen, Arthur L., D.D.S., "Hypersensitivity controlled by iontophoresis: double blind clinical investigation," *The Journal of the American Dental Association*, vol. 68, No. 2 at 216–225 (Feb., 1964).
Schaeffer, Max L. et al., "The Effectiveness of Iontophoresis in Reducing Cervical Hypersensitivity," *Journal of Periodontology*, vol. 42, No. 11 at 695–700 (Nov., 1971).
Brännström, M. et al., "The Hydrodynamics of the Dental Tubule and of Pulp Fluid," *Caries Research*, vol. 1, No. 4 at 310–317 (1967).
Souder, Wilmer, Ph.D. et al., "Experimental Remineralization of Dentin," *The Journal of the American Dental Association*, vol. 31, No. 23 at 1579–1586 (Dec. 1, 1944).
Gangarosa, L.P. et al., "Practical considerations in iontophoresis of fluoride for desensitizing dentin," *The Journal of Prosthetic Dentistry*, vol. 39, No. 1 at 173–178 (Jan., 1978).
Cooley, Robert L. et al., "Effectiveness of potassium oxalate treatment on dentin hypersensitivity," *General Dentistry*, vol. 37, No. 4 at 330–333 (Jul.–Aug., 1989).
Ota, Norio et al., "Effect of Iontophoretic Toothbrush on Cervical Hypersensitvity," __, vol. 5 at 191–199 (1979).
"Dyna–Dental Has Something For You To Smile About" (visited and Printed Feb. 2, 2000) <http://www.ionicbrush.com>.

(List continued on next page.)

Primary Examiner—Kevin Shaver
Assistant Examiner—Melba Bumgarner
(74) Attorney, Agent, or Firm—Fish & Neave; Jeffrey I. Ingerman; Edward M. Arons

(57) ABSTRACT

Iontophoretic devices for treating dentin hypersensitivity are provided. One device includes a housing, an electric current source, and a replaceable cartridge mounted to or in the housing. The cartridge includes (1) a container containing an iontophoretic solution and (2) an applicator assembly fixed to the container. The assembly has a tip portion that is in electrical and fluid communication with the solution. Also provided is an iontophoretic toothbrush that includes an applicator assembly that has a brush with improved bristles.

11 Claims, 6 Drawing Sheets

OTHER PUBLICATIONS

"Clinical Studies Prove HhG's 'Ionic Action' Works Better Than Ordinary Brushing For Plaque Removal" (visited and printed Feb. 2, 2000)<http://www.ionicbrush.com/toothbru.html>.

"U.S. Dental Researchers Report Says: You have a 75% chance of suffering from gum disease" (visited and printed Feb. 2, 2000)<http://www.ionicbrush.com/gumdise.html>.

"What Researchers are saying about the HyG Ionic Toothbrush!" (visited and printed Feb. 2, 2000)<http://www.ionicbrush.com/expert.html>.

Gendusa, Nelson J., D.D.S., Special Report, An Introduction To Fluoride Iontophoresis, How To Relieve Dentin Hypersensitivity In Seconds, *Parkell Today* (Nov., 1999).

* cited by examiner

IONTOPHORETIC APPARATUS

CROSS REFERENCE TO RELATED APPLICATION

This application is a continuation of U.S. patent application Ser. No. 09/658,841, filed Sep. 8, 2000, now abandonded which is hereby incorporated by reference herein in its entirety.

BACKGROUND OF THE INVENTION

This invention relates to iontophoretic devices. More particularly, this invention relates to iontophoretic devices that use electric current to drive ionic species, such as fluoride ions, into hard or soft tissue, including teeth to relieve dentin sensitivity.

According to at least one estimate, as many as 40 million Americans suffer from dentin sensitivity (Cooley, R. L. "Effectiveness of potassium oxilate treatment on dentin hypersensitivity," *Gen Dent.* at 330–333 (July–August 1989)). Moreover, the incidence of hypersensitive dentin is much higher among patients with dentin surfaces exposed by cervical erosion, gingival recession, hypoplasia, or periodontal surgery (Gendusa, N. J. "Special Report, An Introduction To Fluoride Iontophoresis, How To Relieve Dentin Hypersensitivity In Seconds," *Parkell Today* (November 1999)).

According to Brannstron, dentin hypersensitivity may result when fluid movement in open tubules hydraulically stimulates the odontoblasts and nerve fibers at the dentin-pulp junction (Brannstron M, et al., "The Hydrodynamics Of The Dentinal Tubule And of Pulp Fluid, *Caries Res*, 1:310 (1967)).

Gendusa explains that fluoride iontophoresis therapy is known to provide relief from dentin hypersensitivity by driving ionic species into tissue with an electric current. Fendusa also explains that the therapy is based on the principle that similar electric charges repel each other. When sodium fluoride dissolves in an aqueous solution, negatively charged fluoride ions are formed. When a DC circuit is established in a patient's mouth in the presence of such a fluoride solution, such that a cathode is placed in electrical contact with the hypersensitive tissue, the cathode will electrically repel the fluoride ions into the tooth surface. According to Souder, the fluoride ions react with the calcium in the hydroxyapatite of the dentin to form fluorapatite ($CaF_2$), which is believed to block the tubules with an insoluble compound (Souder W, et al., "Experimental Remineralization Of Dentin," *J. Am. Dent. Assoc.* 31:1579 (1944)).

A number of chair-side fluoride iontophoresis delivery systems are known, including one sold under model No. D643D, available from Parkell, Electronics Division, of Farmingdale, N.Y. The system includes: (1) a battery-operated dentist-held device, (2) a patient-held grounding device, and (3) an electrically conductive cord connecting the two devices.

The dentist-held device includes a cathodic probe, which is metal, through which electric current can be applied to a patient's tooth. Before being operated, however, the metal probe is inserted with a cotton pledget into a disposable plastic tube. During operation, an aqueous sodium fluoride solution is applied to the cotton permitting electric current to flow inside the plastic tube from the metal probe to the tooth.

Although the plastic tube and the cotton pledget are disposable, the metal probe is not, which means that it must be sterilized between patients. Such cleaning is costly, time consuming, and introduces a risk of infection if the probe is not properly sterilized.

Iontophoretic toothbrushes are also known, but they are relatively inefficient. The problem is that during normal brushing, the entire mouth is wet by a mixture of toothpaste, water, and saliva. This wet condition normally causes a substantial portion of the electrical current to be directed away from the intended treatment area because the electric current flows along the path of least resistance. Moreover, the magnitude of the electric current applied during an iontophoresis treatment can be limited to the degree of dentin sensitivity.

It would therefore be desirable to provide an iontophoretic toothbrush that efficiently directs electric current toward an intended area, even when the mouth is wet.

It would also be desirable to provide an iontophoresis device that does not require sterilization between patients.

It would further be desirable to provide an iontophoresis device that reduces the amount of time required for an iontophoretic treatment.

It would be still more desirable to provide an iontophoresis device that permits relatively large electric currents to be used during an iontophoretic treatment.

SUMMARY OF THE INVENTION

It is an object of this invention to provide an iontophoretic toothbrush that efficiently directs electric current toward an intended area, even when the mouth is wet.

It is also an object of this invention to provide an iontophoresis device that does not require sterilization between patients.

It is a further object of this invention to provide an iontophoresis device that reduces the amount of time required for an iontophoretic treatment.

It is a still a further object of this invention to provide an iontophoresis device that permits a patient to withstand larger electric current during an iontophoretic treatment.

In accordance with this invention, there is provided an iontophoretic apparatus that includes a replaceable cartridge. The replaceable cartridge can be mounted to a handle of the iontophoretic apparatus and includes a container containing an iontophoretic solution, and an applicator assembly fixed to the container that is in electrical communication with said solution in the container.

The replaceable nature of the cartridge eliminates the need to sterilize the applicator assembly each time a patient is treated. Thus, the cartridge is preferably disposable, although, as described below, it can be constructed to be refillable. In any case, the applicator assembly is preferably disposable. The cartridge also supplies a sterile iontophoretic solution to the applicator portion of the applicator assembly during operation. Cartridges having solutions of different concentrations can be provided, as desired.

According to another aspect of this invention, an iontophoretic toothbrush is provided. The iontophoretic toothbrush includes a handle, an electric current source, and an applicator assembly. The handle has an outer surface that is electrically conductive. The electric current source preferably supplies a regulated electric current using, for example, a power source (e.g., a battery), a regulator circuit, and a fuse. The applicator assembly is fixed to the handle and includes a tip portion that includes a brush having a plurality of bristles. Each of the bristles includes (1) an electrically conductive core having a first electrical resistance, and (2) a sheath around the core having a second electrical resistance that is greater than the first electrical resistance. Methods for making and using these apparatus are also provided.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which.

DETAILED DESCRIPTION OF THE INVENTION

In order that the invention herein described may be fully understood, the following detailed description is set forth.

According to one aspect of the present invention, an iontophoretic apparatus that includes a replaceable cartridge is provided. The replaceable cartridge can be mounted to a handle of the iontophoretic apparatus and includes (1) a container containing an iontophoretic solution and (2) an applicator assembly fixed to the container that is in electrical communication with said solution in the container.

The replaceable nature of the cartridge eliminates the need to sterilize the applicator assembly each time a patient is treated. Thus, the entire cartridge can be disposable, although the cartridge can be constructed so that the container is refillable. In any case, the applicator assembly is preferably disposable. As explained more fully below, during operation of the apparatus, the cartridge supplies a sterile iontophoretic solution to a tip portion of the applicator assembly. Cartridges can be provided that have different types or concentrations of solutions.

According to another aspect of this invention, an iontophoretic toothbrush is provided. The iontophoretic toothbrush includes a handle, an electric current source, and an applicator assembly. The handle has an outer surface that is electrically conductive. The electric current source preferably supplies a regulated electric current using, for example, a power source (e.g., a battery), a regulator circuit, and a fuse. The applicator assembly is fixed to the handle and includes a tip portion that includes a brush having a plurality of bristles. Each of the bristles includes (1) an electrically conductive core having a first electrical resistance, and (2) a sheath around the core having a second electrical resistance that is greater than the first electrical resistance. The bristle construction forces electric current to flow through the core of the bristle to surface of a tooth and prevents the electric current from being shunted in the aqueous solution that is found in the mouth during tooth brushing. This construction is believed to substantially increase the effectiveness of the toothbrush.

Figure 1:
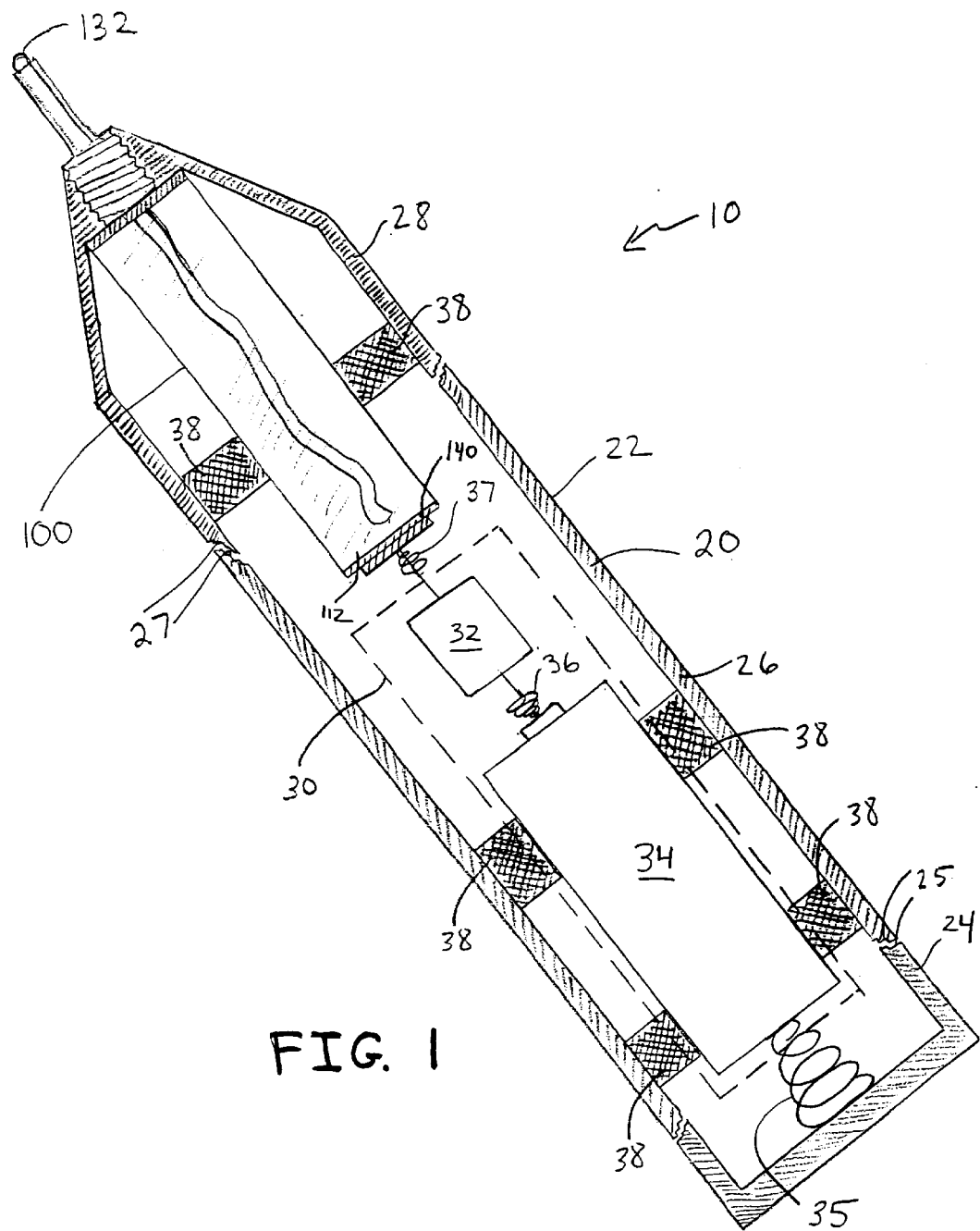
FIG. 1 shows an illustrative iontophoretic apparatus, partially in cross section, including an illustrative iontophoretic cartridge, according to this invention.

FIG. 1 shows illustrative iontophoretic apparatus 10 according to this invention. Apparatus 10 includes, among other things, housing 20, electric current source 30, and replaceable cartridge 100. Housing 20 can have any external shape convenient for hand-held operation and preferably has an external surface portion 22 that is electrically conductive. Electric current source 30 supplies a regulated electric current appropriate for performing iontophoresis. Replaceable cartridge 100 is mounted to housing 20 and includes container 110, which contains an iontophoretic solution, and applicator assembly 130, which is fixed to container 110. The construction of replaceable cartridge 100 is described more fully below.

Electric current source 30 preferably includes electric current regulator circuit 32, which can include a fuse that prevents the electric current from exceeding a maximum electric current. The magnitude of the regulated current can be user selectable or predetermined. Electric current source 30 can further include power source 34, which provides power to regulator circuit 32. Power source 34 can be a replaceable or rechargeable battery. It will be appreciated that current source 30, regulator circuit 32, and power source 34 are only schematically represented by boxes. It will be further appreciated that the shape and configuration of apparatus 10 and its components are illustrative only and can be changed as desired.

The electric current used to perform iontophoresis can be an alternating electric current or a direct electric current. If it is alternating, it preferably has a frequency between about 0.01 Hz and about 1 MHZ. A typical iontophoretic treatment using direct electric current lasts a few minutes at a current of less than about 1.0 milliamp. It is believed that shorter treatment times are possible using alternating electric currents because patients will be less sensitive to alternating electric currents than direct electric currents. Lower sensitivity allows for larger applied electric currents, thereby reducing treatment times.

Housing 20 can be formed from two or more connectable components. For example, housing 20 includes proximal component 24, intermediate component 26, and distal component 28. These components can be releasably fastened using any convenient means, such as threaded surfaces 25 and 27. This multi-component housing facilitates replacement of the cartridge and/or a battery.

When apparatus 10 is held by the patient, and the tip portion is inserted into the patient's mouth, a closed electric circuit is formed. The electric current flows from source 34, through circuit 32, through replaceable cartridge 100 to tip 132, through the tooth and/or gum region around the tooth, through the body of the patient being treated, through the patient's hand, and back into source 30 through housing 20. When a dentist holds apparatus 10 during operation, the electric current path is substantially the same as described above, except that the dentist will be included in the electric path—not the patient's hand. To ensure proper electric current flow, tip 132 is preferably electrically isolated from housing 20, except as described.

It will be appreciated that the electric current source need not be inside the housing. For example, the electric current source can be located outside the housing and connected to the housing via an insulated electric cord. In this case, the patient may be asked to make contact with an electrically conductive element (e.g., a metallic grip) that is connected to the external current source.

In one embodiment, outer surface 22 of housing 20 has an electrically conductive portion. That portion is electrically connected to electrical contact 35, which can be in the form of an elastic spring. Electrical contacts 36 and 37 can also be used to ensure proper electrical connections between power source 34 and circuit 32 and between circuit 32 and cartridge 100. All internal components can be supported by one or more support structures 38.

It will be appreciated that electrical contact 37 need not make an electrical connection with cartridge 100 near proximal end 112 (e.g., cap 140). Alternatively, the electrical connection can be made anywhere on cartridge 100 with any conductive structure capable of conducting electricity to the solution contained in cartridge 100.

Figure 2:
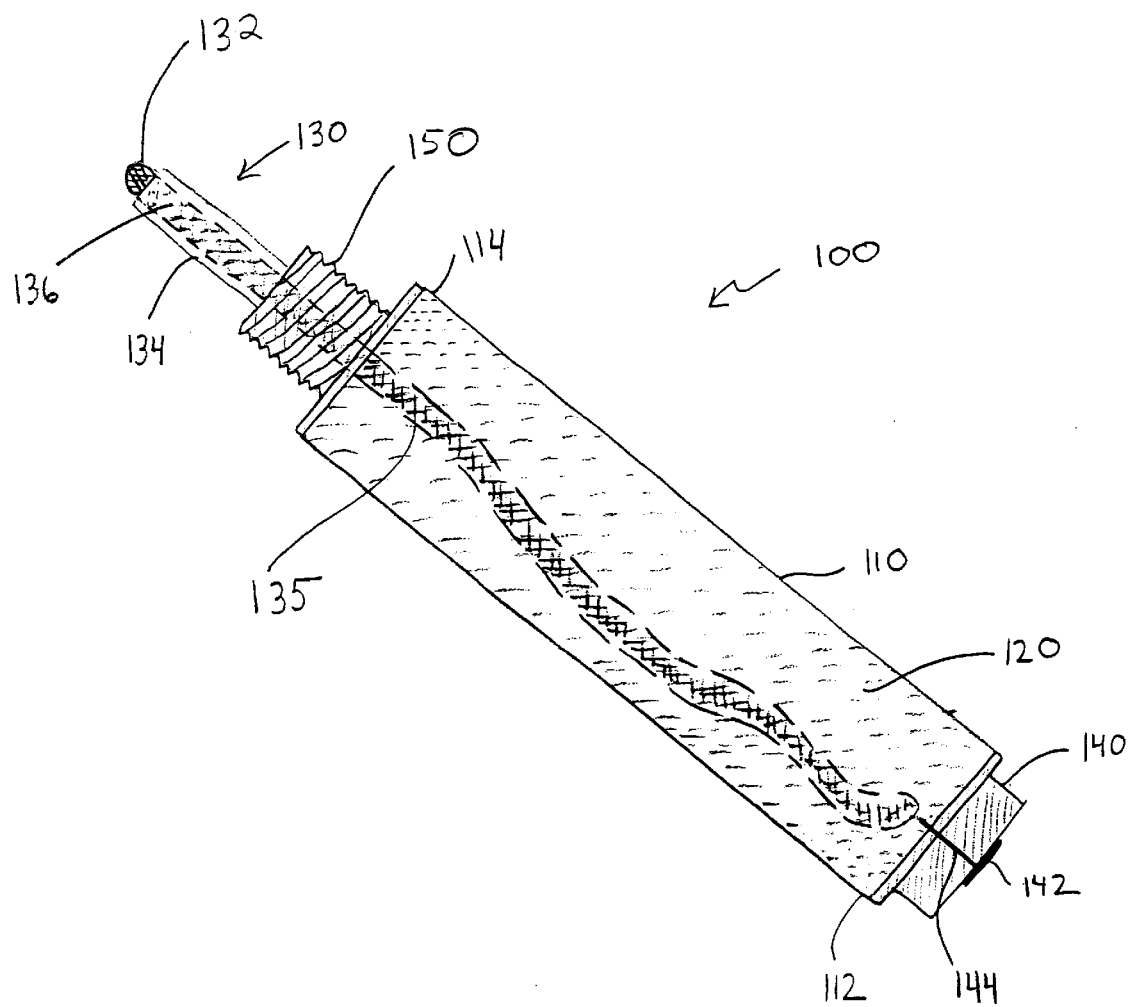
FIG. 2 shows the illustrative iontophoretic cartridge, partially in cross section, shown in FIG. 1, according to this invention.

FIG. 2 shows one illustrative embodiment, partially in cross section, of the replaceable cartridge 100 shown in FIG. 1. Cartridge 100 includes container 110, which contains iontophoretic solution 120, and applicator assembly 130, which is fixed to container 110. Applicator tip 132 of assembly 130 is in electrical communication with solution 120 through, for example, wick 135.

In one embodiment, container 110 is permanently fixed to applicator assembly 130. In this case, cartridge 110 is preferably disposable. In another embodiment, container 110 is detachable from to applicator assembly 130. In this case, container 110 can be reused and refillable with solution.

Container 110 preferably has at least one electrically conductive portion that provides an electrical connection between solution 120 and the electric current source. For example, the electrically conductive portion may be container 110 itself. Alternatively, electrically conductive portion may be cap 140 or a portion of cap 140. According to another embodiment, container 110 may be electrically insulating, but include an electrically conductive wire (or a passageway containing the solution) that extends into container 110 and attaches to an electrically conductive surface of container 110. Cap 140, for example, can include electrically conductive structure 144 that electrically couples surface 142 to solution 120.

Figure 3:
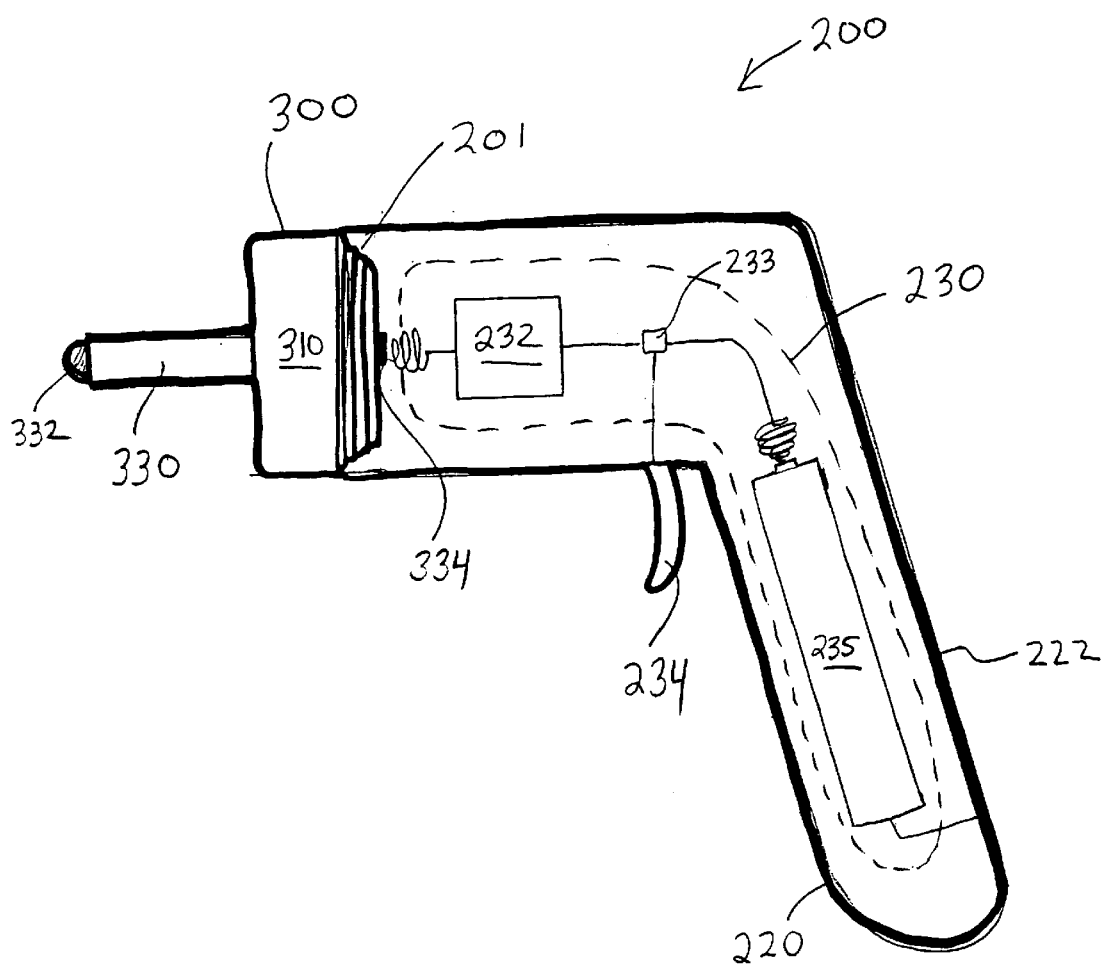
FIG. 3 shows another illustrative iontophoretic apparatus, partially in cross section, including another illustrative iontophoretic cartridge, according to this invention.

Container 110 can include a fastener for mounting cartridge 100 to an iontophoretic apparatus. Container 110 includes fastener 150, which can be a threaded surface. Thus, as shown in FIG. 2, for example, threaded surface 150 can be used to mount cartridge 100 to iontophoretic apparatus 10 by simply screwing cartridge 100 to housing 20. The threads can either be provided to outwardly oriented surface of cartridge 110 (as shown in FIG. 1) or to an internally facing surface. As best shown in FIGS. 1 and 3, a cartridge according to this invention can be operationally mountable in or near a distal end of the iontophoretic apparatus.

Cartridge 100 can further include an electrical connector between solution 120 and applicator tip 132. As shown in FIG. 1, for example, the electrical connector can be wick 135. Wick 135 is at least partially in contact with and capable of conducting solution 120. It will be appreciated that applicator tip 132 can be the distal end of wick 135 or it can be an entirely separate item that is in electrical and fluid communication with wick 135. For example, tip portion 132 can be a brush, a fibrous swab, a felt-like tip, or any combination thereof.

Applicator assembly 130 can include tubular structure 134, which has longitudinal passageway 136. In this case, wick 135 is located in passageway 136 and is in contact with and capable of conducting solution 120 to tip portion 132. Alternatively, as shown best in FIG. 3, applicator assembly 130 can include a tubular structure having a longitudinal passageway and a ball rotatably retained at one end of the passageway. Thus, applicator assembly 130 has solution channel (e.g., passageway 136) for passing solution from inside container 110 to a place near a surface of a tooth.

As shown in FIG. 1, for example, container 110 can be a substantially cylindrical structure having proximal end 112 and distal end 114, In this case, applicator assembly 130 is fixed, possibly removably fixed, to distal end 114. Proximal cap 140 can be used to plug proximal end 112.

The iontophoretic solution can be any solution used to perform iontophoresis. For example, some of the solutions that can be used according to this invention are a sodium fluoride solution, a calcium fluoride solution, strontium chloride solution, a sodium monofluorophosphate solution, and any combination of these solutions. Preferably, the solution has a fluoride salt concentration less than about 5.0% by weight. The solution can include one or more additional ingredients, such as abrasives or tooth whiteners. The solution can also be in the form of a gel.

FIG. 3 shows another illustrative iontophoretic apparatus 200 according to this invention. Apparatus 200 includes, among other things, housing 220, electric current source 230, and replaceable cartridge 300. Housing 220 can have any external shape convenient for hand-held operation, which in this case has the shape of a gun. Housing 220 can have external surface portion 222 that is electrically conductive. Alternatively, the external surface portion can be insulating, as long as an electrical connection can be made with the patient in some other way (e.g., via an electrically connecting cord). Electric current source 230 supplies a regulated electric current appropriate for performing iontophoresis. Replaceable cartridge 300 is mounted to distal end 201 of housing 220 and includes container 310, which contains an iontophoretic solution, and applicator assembly 330.

The construction of replaceable cartridge 300 is similar to cartridge 100 described above. The main difference between cartridges 100 and 300 is applicator tips and the ways the cartridges are mounted to their respective housings 20 and 220, respectively. In particular, cartridge 100 includes a wick while cartridge 300 includes ball retained at the tip. Also, cartridge 100 is mounted substantially inside housing 20 while cartridge 300 is mounted substantially outside and at the distal end of housing 220.

Figure 5:
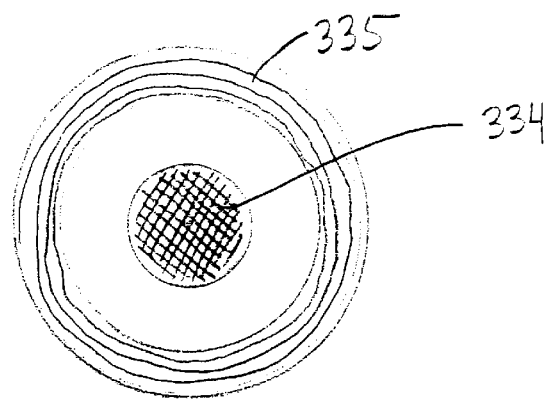
FIG. 5 shows a back view of the illustrative iontophoretic cartridge shown in FIG. 4, partially in cross section, taken from line 5—5 of FIG. 4, according to this invention.
Figure 4:
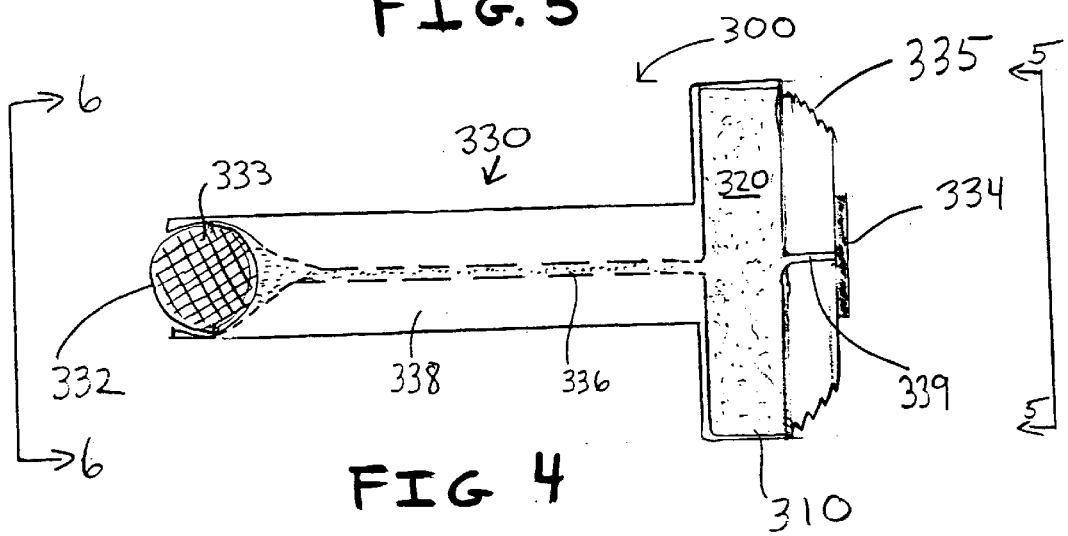
FIG. 4 shows the illustrative iontophoretic cartridge, partially in cross section, shown in FIG. 3, according to this invention.
Figure 6:
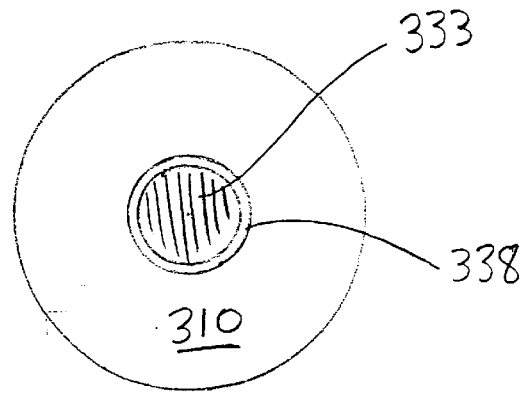
FIG. 6 shows a front view of the illustrative iontophoretic cartridge shown in FIG. 4, partially in cross section, taken from line 6—6 of FIG. 4, according to this invention.

FIGS. 4–6 show cartridge 300 from three different views.

FIG. 4 is a side view, partially in cross section, of cartridge 300. As shown in FIG. 4, cartridge 300 includes at least container 310, which contains iontophoretic solution 320, and applicator assembly 330, which is fixed to container 310. Applicator tip 332 of assembly 330 is ball 333. Tip 332 is in electrical communication with solution 320 through passageway 336 formed in elongated tubular structure 338. Also, passageway 339, which opens to conductive element 334, electrically connects element 334 to solution 320.

FIG. 5 is a back view of cartridge 300 taken along line 5—5 of FIG. 4. FIG. 5 best shows conductive element 334 and threaded surface 335 for mounting cartridge 300 to apparatus 200. FIG. 6 is a front view of cartridge 300 taken along line 6—6 of FIG. 4. FIG. 6 best shows the front surface of ball 333 and retaining portion of tubular structure 338.

Assembly 300 also includes electrically conductive element 334 for making an electrical connection with regulator circuit 232 of apparatus 200. In addition to circuit 232, electrical current source includes switch 233, which is controlled by trigger 234, and power source 235.

Figure 7:
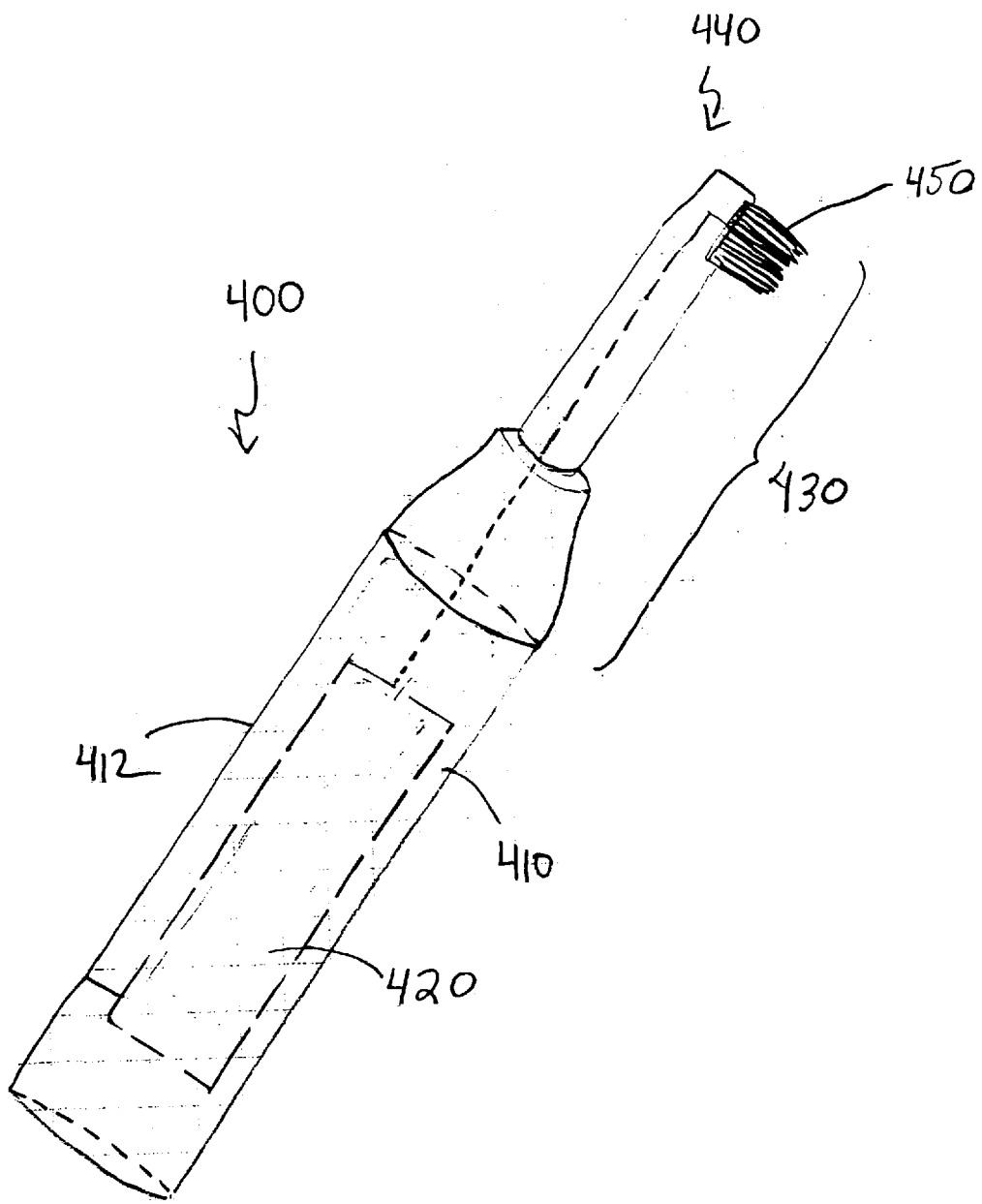
FIG. 7 shows a simplified perspective view, partially in cross-section, of an illustrative iontophoretic toothbrush according to this invention.

According to another aspect of this invention, an iontophoretic toothbrush is provided with improved bristles. FIG. 7 shows illustrative iontophoretic toothbrush 400, which includes housing 410, electrical current source 420, and applicator assembly 430. Housing 410 has outer surface 412 that is electrically conductive and transmits electric current to source 420 during operation when held within a user's hand. Electric current source 420 supplies a regulated electric current and is substantially similar to the one describe above. Regulation can be either current or voltage based. Applicator assembly 430 is fixed to housing 410 and includes tip portion 440 that includes brush 450. Brush 450 includes a plurality of bristles 460.

Figure 8:
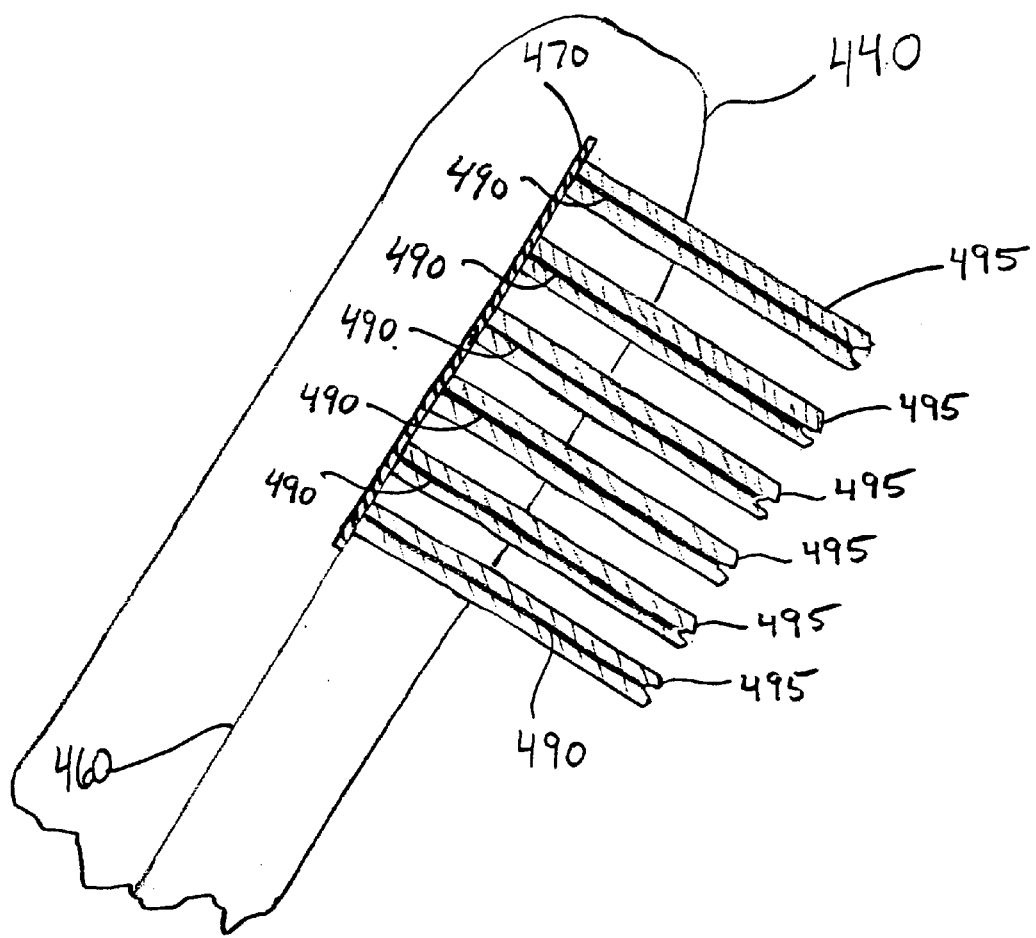
FIG. 8 shows a more detailed perspective view of the tip portion of the illustrative iontophoretic toothbrush shown in FIG. 7 according to this invention.
Figure 1:
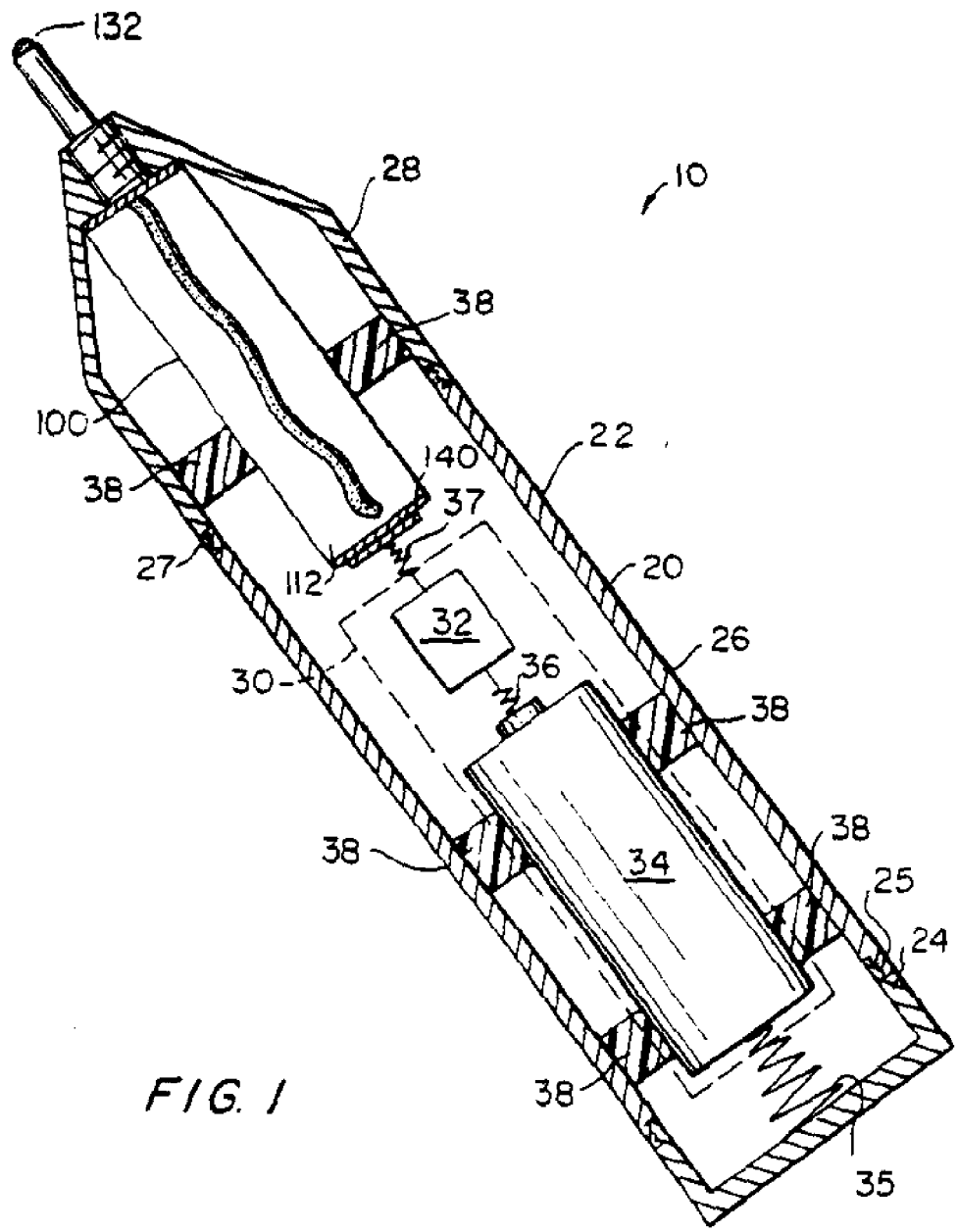
Figure 2:
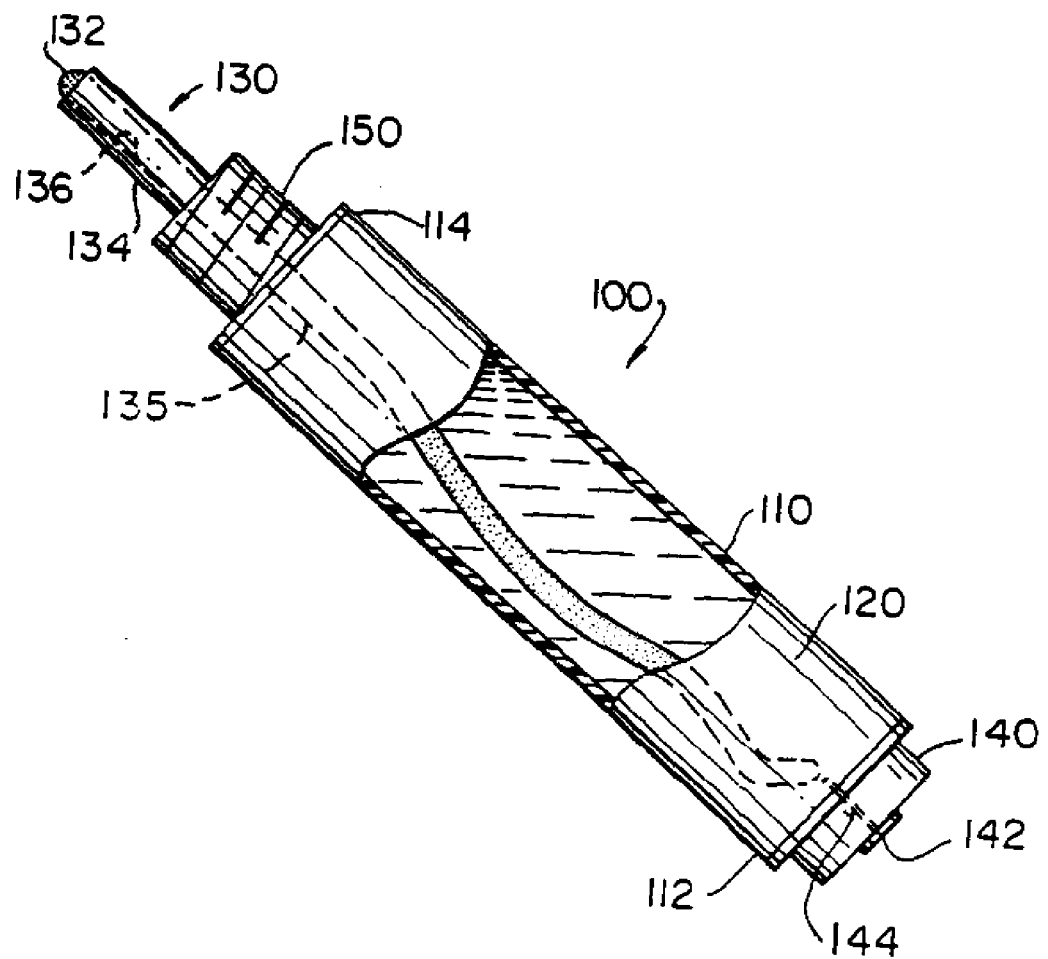
Figure 3:
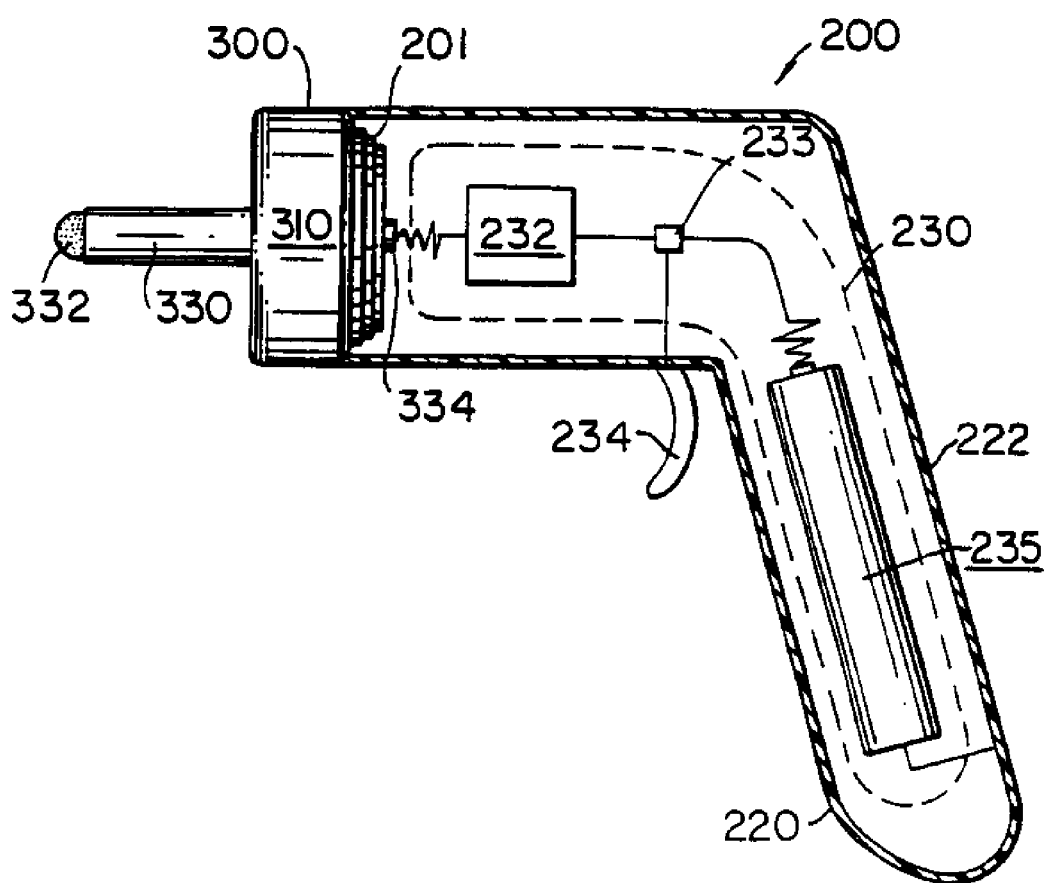
Figure 5:
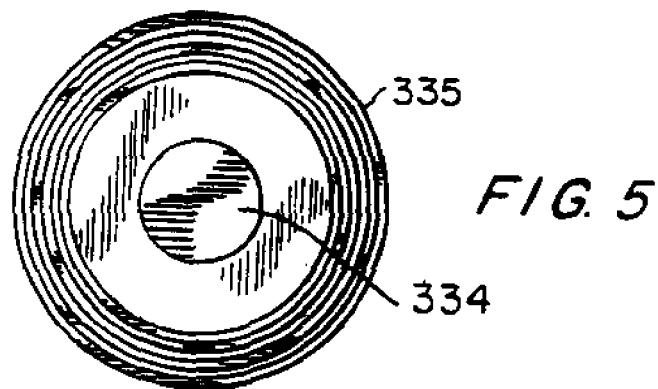
Figure 4:
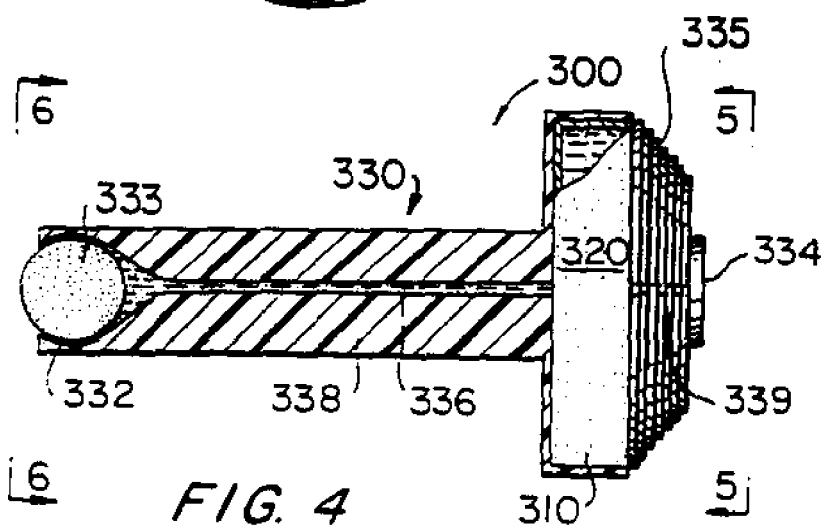
Figure 6:
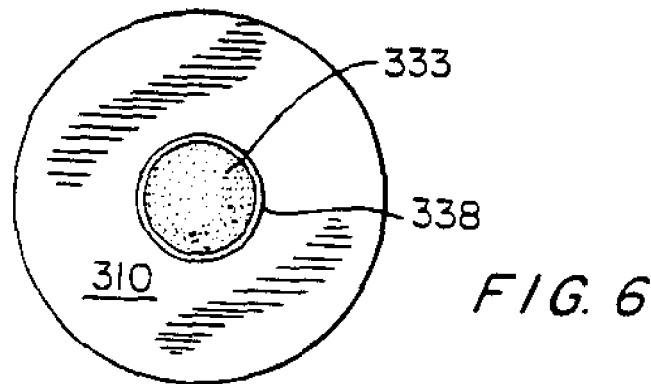
Figure 7:
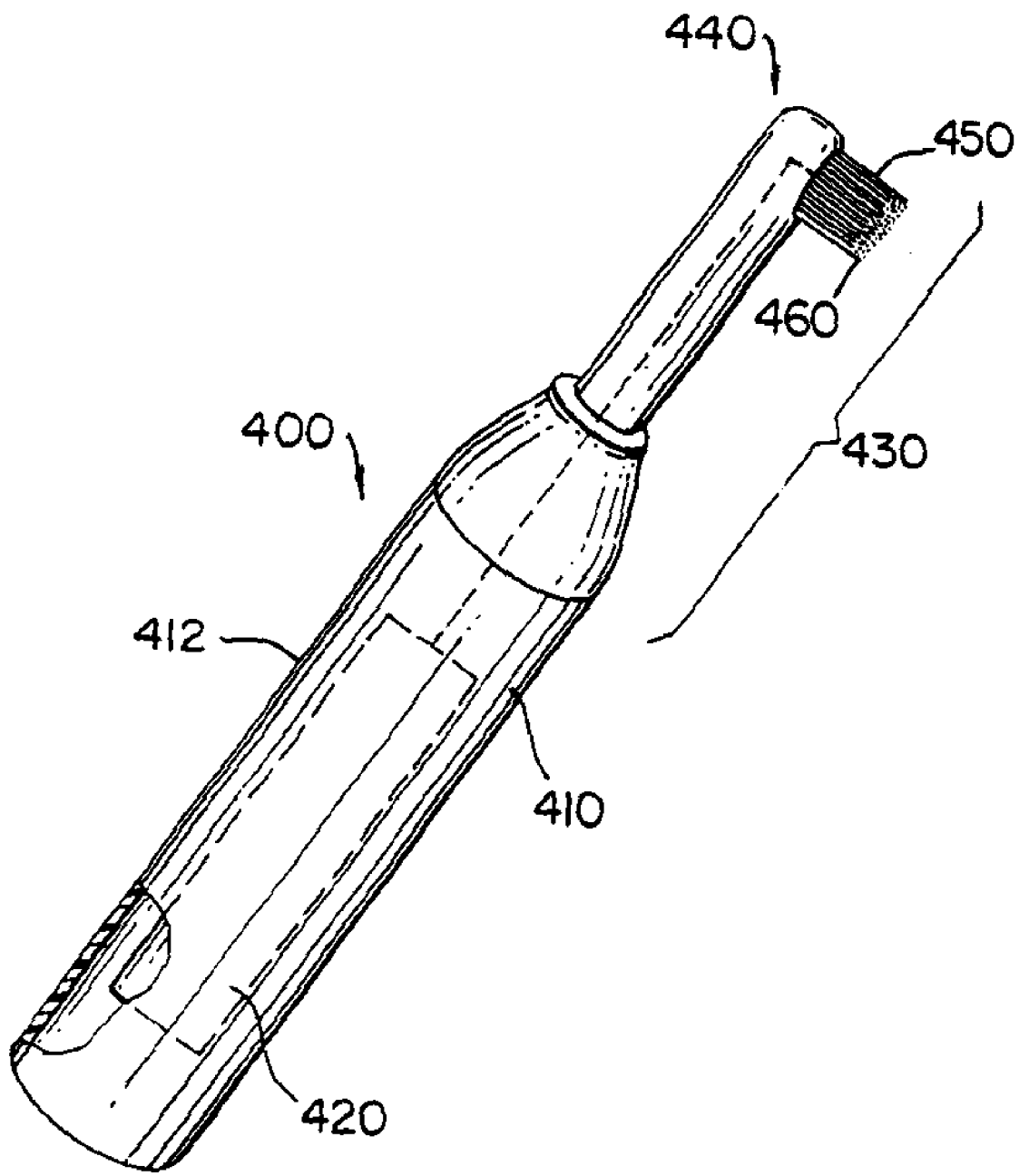
Figure 8:
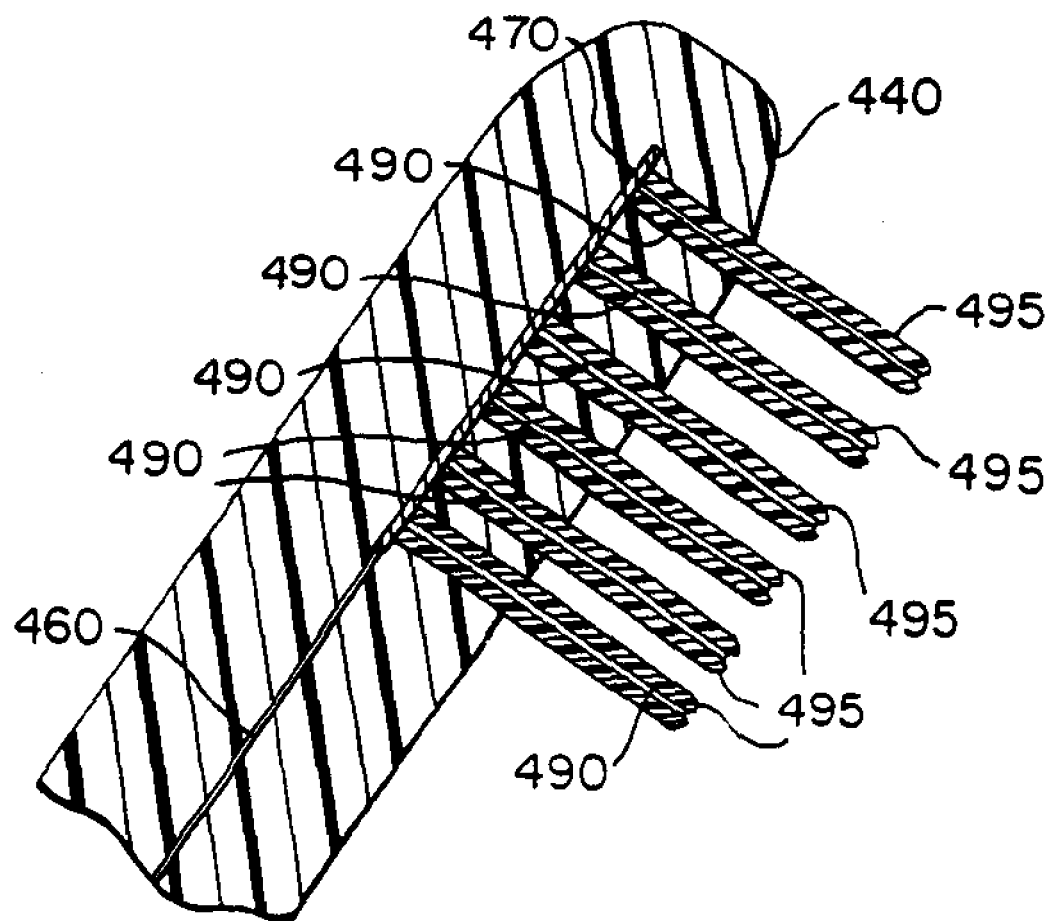
Figure 1:
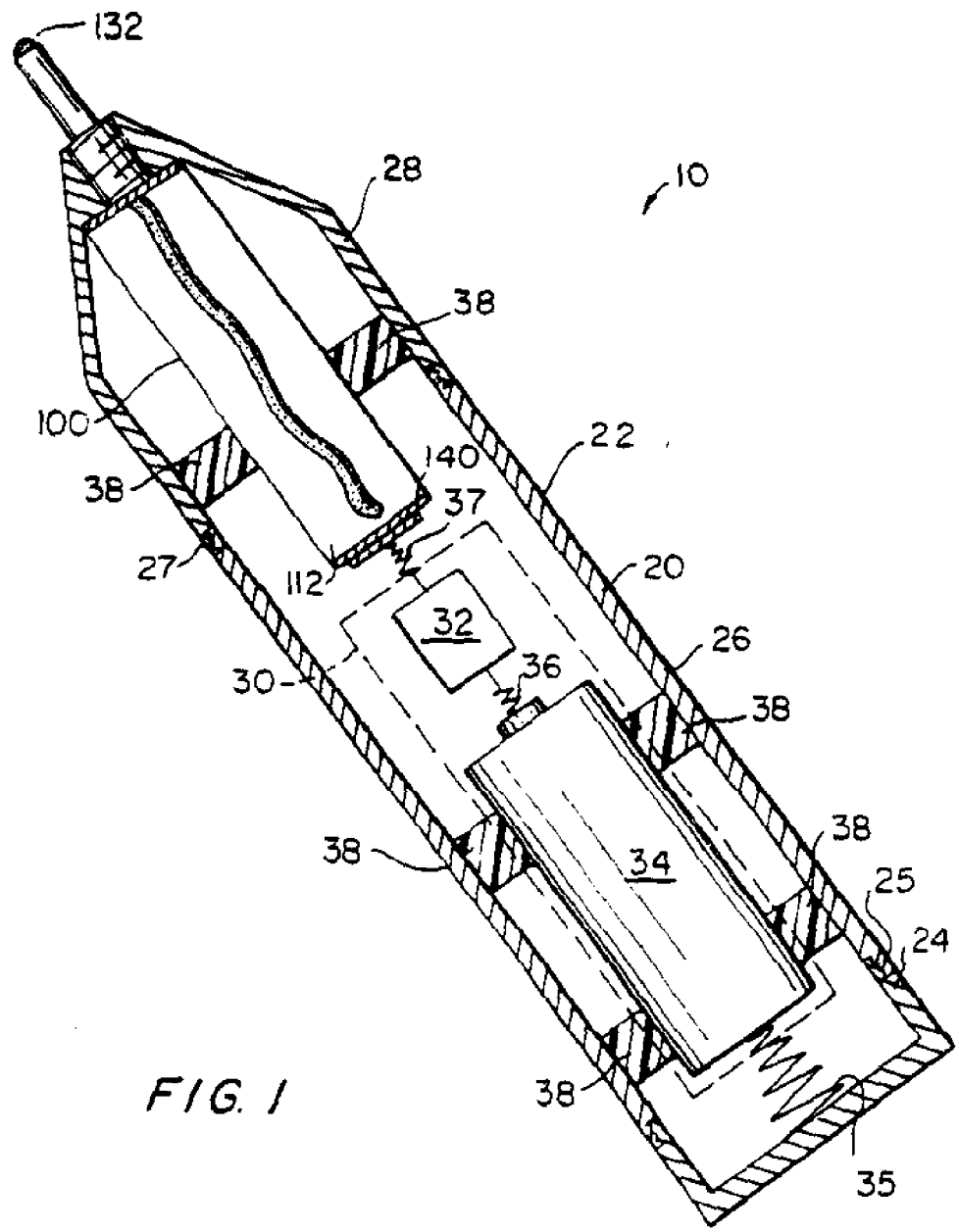
Figure 2:
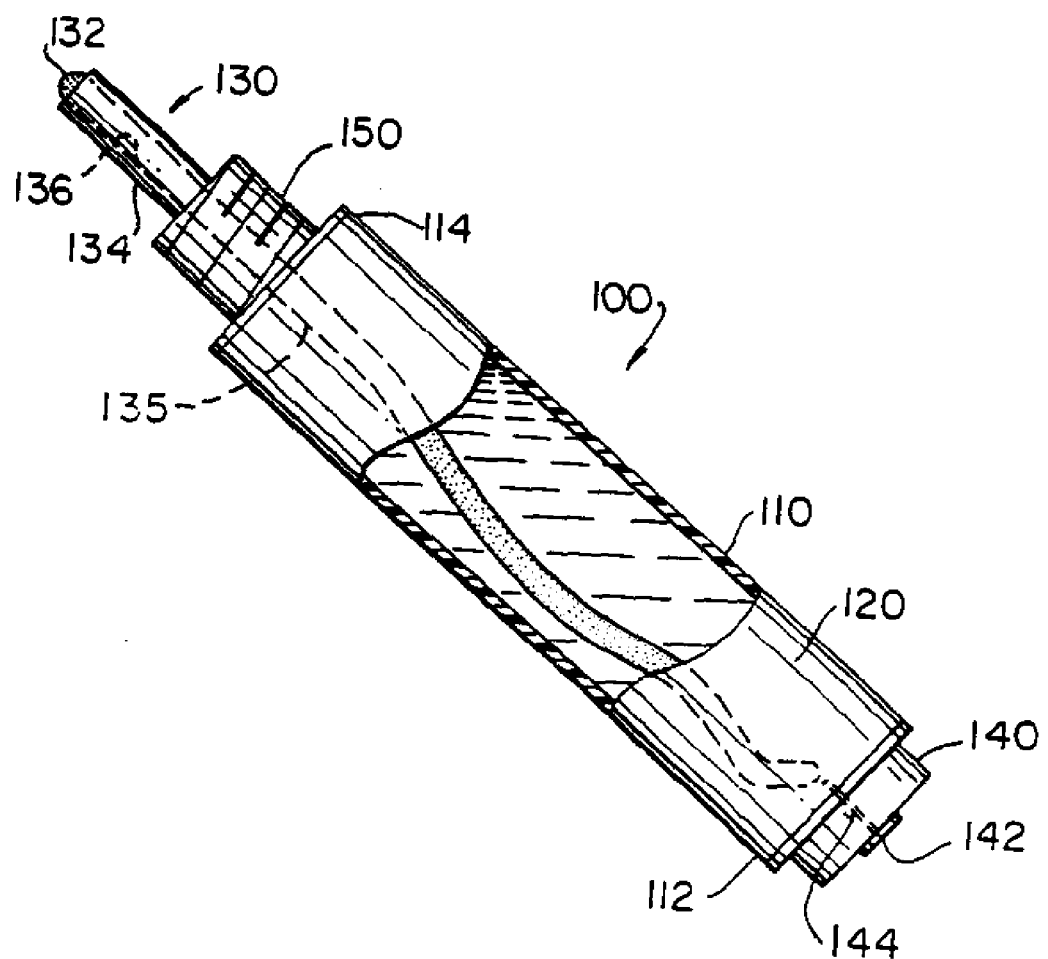
Figure 3:
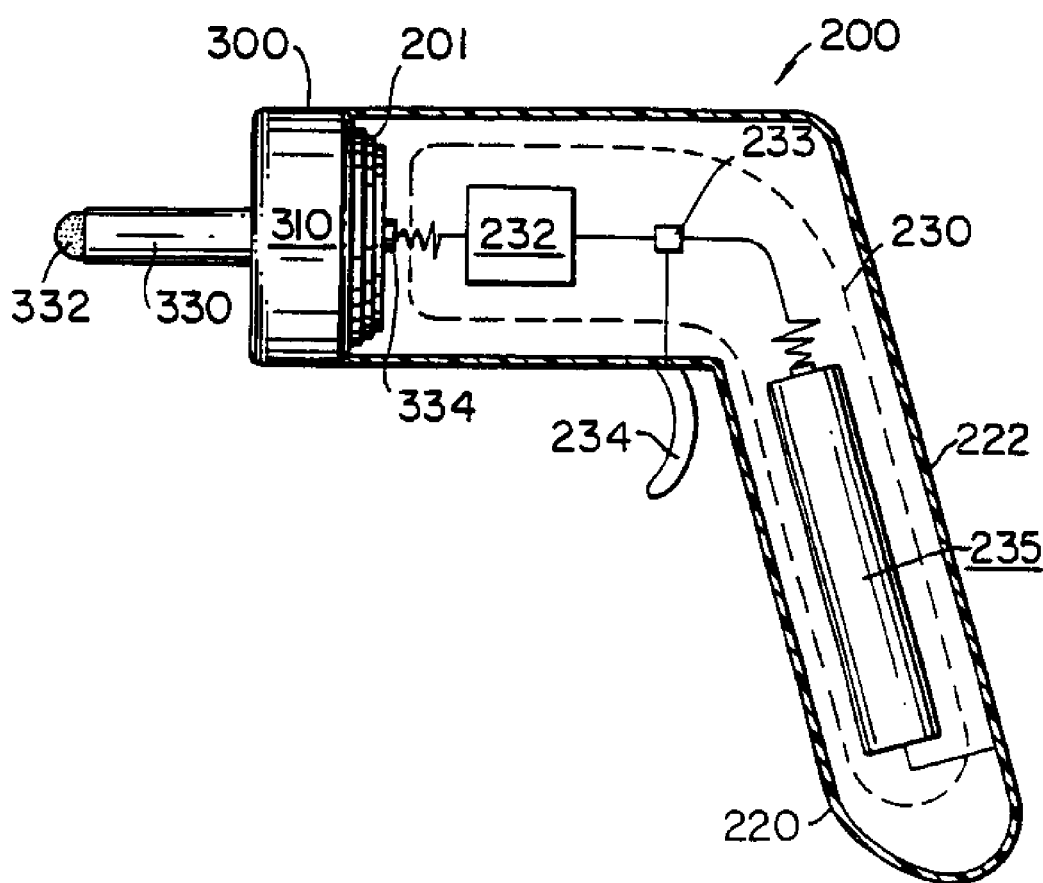
Figure 5:
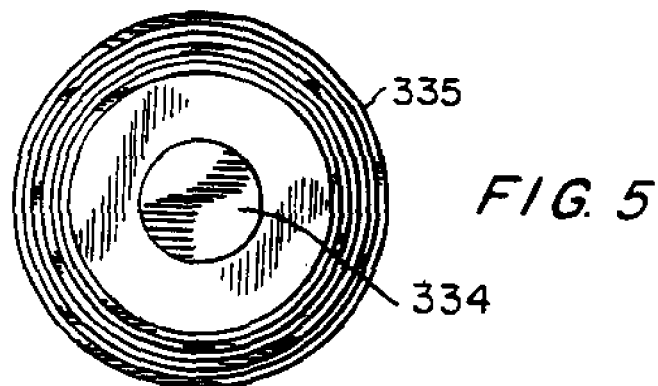
Figure 4:
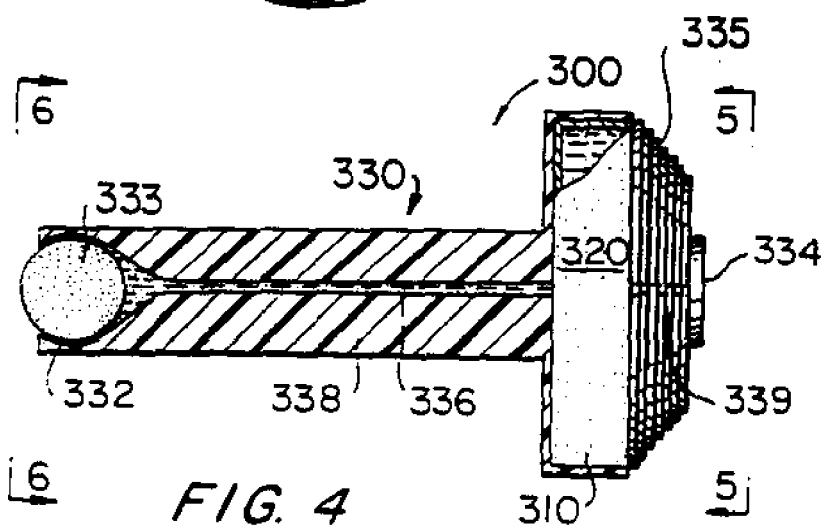
Figure 6:
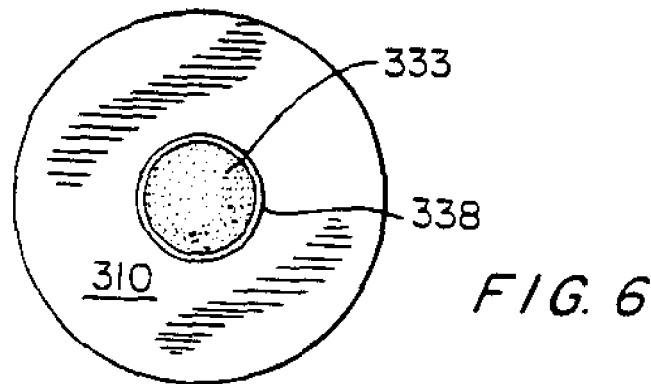
Figure 7:
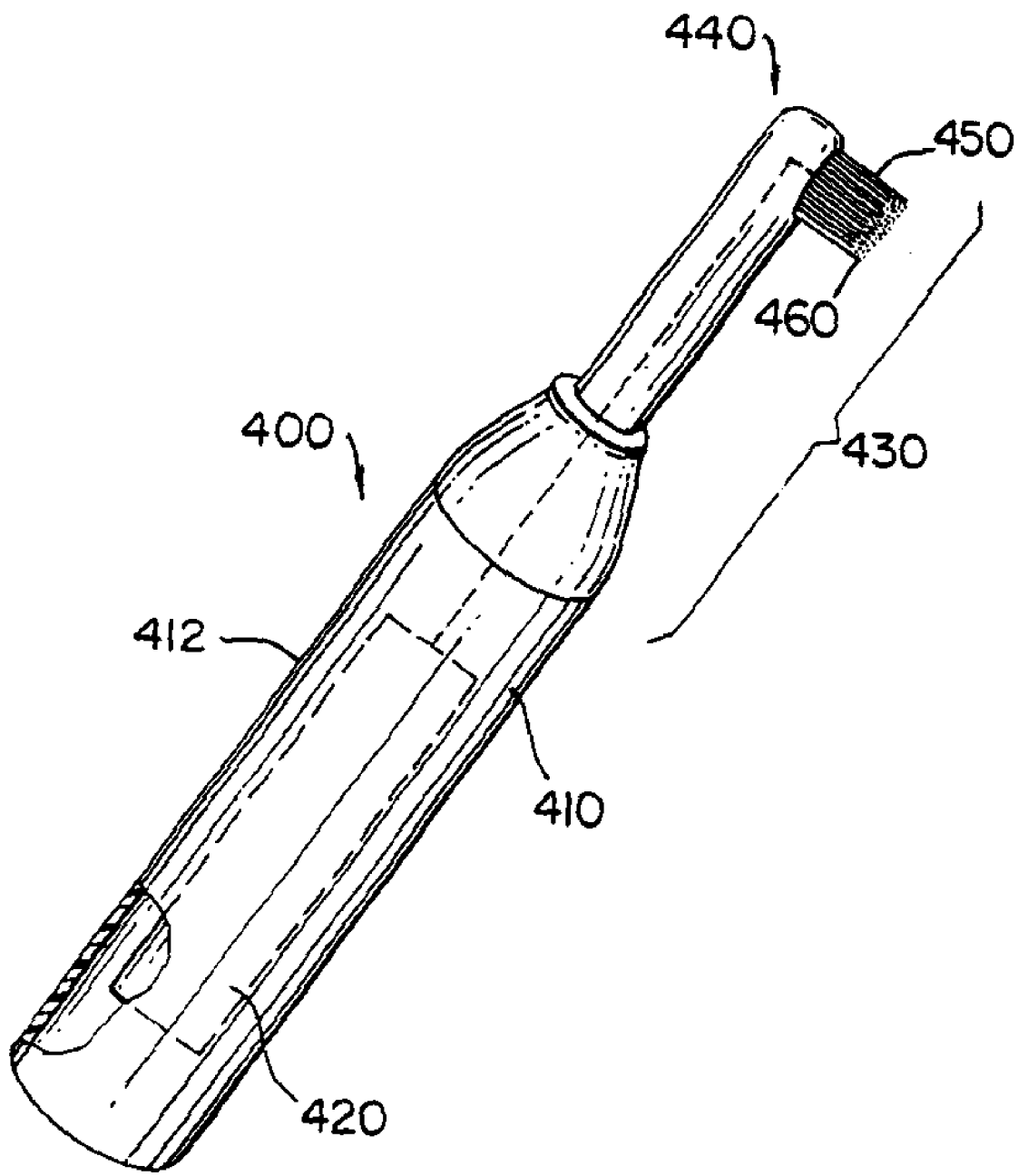
Figure 8:
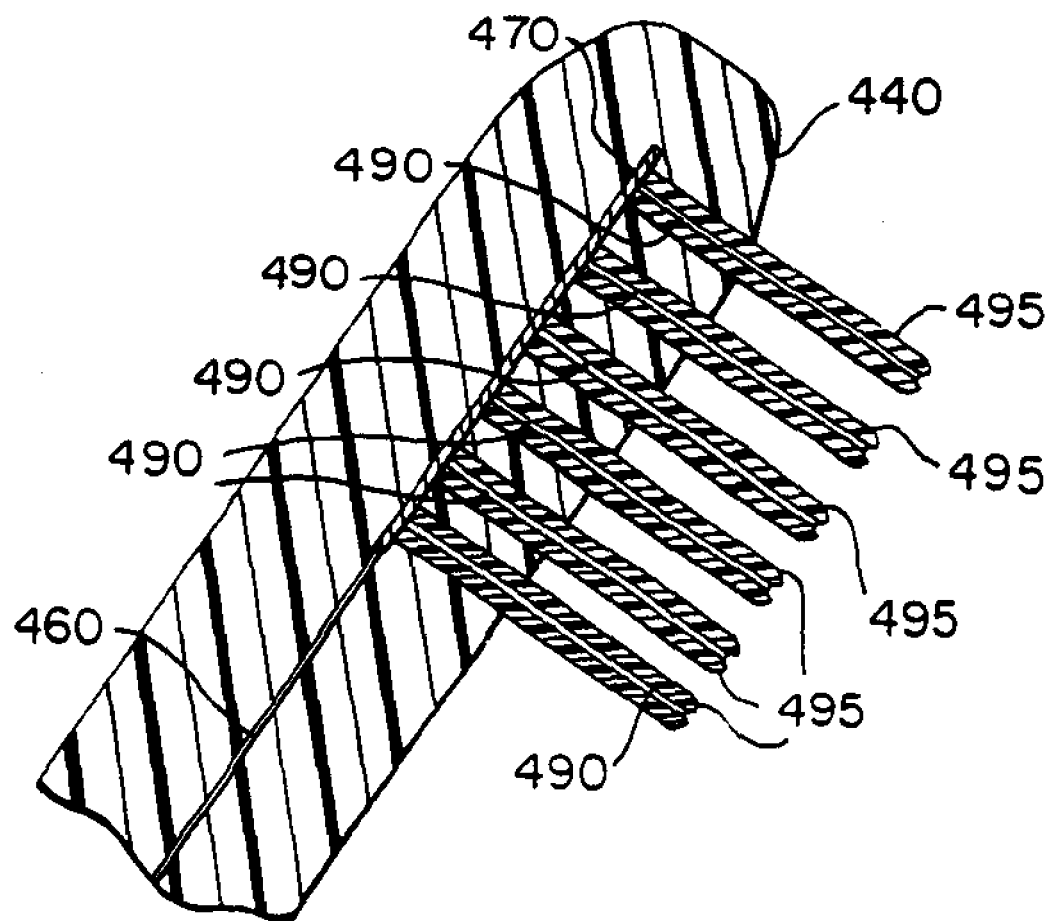

As shown best in FIG. 8, each bristle includes: (1) electrically conductive core 490 having a first electrical resistance and (2) sheath 495 around core 490 having a second electrical resistance that is greater than the first electrical resistance. Core 490 of each bristle is electrically connected to electrical current source 420 via conductive element 460 and, optionally, plate 470. Core 490 can be made from an electrically conductive polymer or from a metallic material. If the core is made from a metallic material, the length of the core can be less than the length of the surrounding sheath to prevent direct contact between the core and a tooth during brushing, especially after extended use. Sheath 495 can be made from any substantially electrically insulating polymer.

Thus it is seen that an improved iontophoretic apparatus, with several variations, has been provided. The apparatus is efficient and virtually eliminates the risk of infection without sterilization procedures. One skilled in the art will appreciate that this invention can be practiced by other than the described embodiments, which are presented for purposes of illustration and not of limitation, and this invention is limited only by the claims which follow.

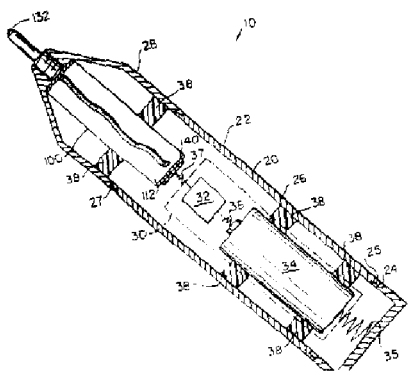

What is claimed is:

1. An iontophoretic apparatus comprising:

an iontophoretic solution contained inside a container, said container comprising a base and having a mouth set apart, along a longitudinal direction, from said base;

an electric current source in electrical communication with said solution;

an applicator tip in contact with said solution;

an elongated wicking element having a first end and a second end, said wicking element elongated along said longitudinal direction, said first end immersed in said solution, said second end configured to deliver said solution to a point outside of said container; and an applicator assembly configured to support said applicator tip and fixed to said container.

2. The apparatus of claim 1 wherein said applicator tip and said applicator assembly are disposable.

3. The apparatus of claim 2 wherein said electric current source is an alternating electric current source.

4. The apparatus of claim 2 within said wicking element is in electrical communication with said solution and said applicator tip.

5. The apparatus of claim 2 wherein:

said applicator assembly comprises a tubular structure having a longitudinal passageway; and said applicator tip comprises a ball rotatably retained at one end of said passageway.

6. The apparatus of claim 2 wherein said applicator tip is selected from the group consisting of a fibrous swab, bristles, a felt-like tip, and any combination thereof.

7. The apparatus of claim 1 wherein said applicator assembly is permanently fixed to said container.

8. The apparatus of claim 2 wherein said electric current source is an alternating electric current source.

9. The apparatus of claim 2 wherein said wicking element is in electrical communication with said solution and said applicator tip.

10. The apparatus of claim 2 wherein:

said applicator assembly comprises a tubular structure having a longitudinal passageway; and said applicator tip comprises a ball rotatably retained at one end of said passageway.

11. The apparatus of claim 2 wherein said applicator tip is selected from the group consisting of a fibrous swab, bristles, a felt-like tip, and any combination thereof.

* * * * *

UNITED STATES PATENT AND TRADEMARK OFFICE
CERTIFICATE OF CORRECTION

PATENT NO. : 6,743,015 B2
DATED : June 1, 2004
INVENTOR(S) : Thomas J. Magnani

It is certified that error appears in the above-identified patent and that said Letters Patent is hereby corrected as shown below:

Title page should be deleted and substitute therefor the attached title page.

Drawings consisting of FIGS. 1-8 should be deleted to appear as per the attached sheets.

Title page,
Item [56], References Cited, OTHER PUBLICATIONS,
"Ota, Norio et al.," reference, "Hypersensitvity" should be -- Hypersensitivity --.
"Gendusa, Nelson J., D.D.S.," reference, "Special" should be -- "Special --; "Seconds" should be -- Seconds" --.

Column 1,
Line 8, "abandonded" should be -- abandoned --.
Line 31, "Brannstron" should be -- Brannstron, --.
Line 48, "Souder" should be -- Souder, --.

Column 4,
Line 7, after "to", should be inserted -- the --.

Column 5,
Line 32, "cartridge 110" should be -- cartridge 100 --.
Line 34, "to" should be deleted.
Line 58, "cartridge 110" should be -- cartridge 100 --.

Signed and Sealed this

Twenty-second Day of March, 2005

JON W. DUDAS
*Director of the United States Patent and Trademark Office*

(12) United States Patent
Magnani

(10) Patent No.: US 6,743,015 B2
(45) Date of Patent: Jun. 1, 2004

(54) IONTOPHORETIC APPARATUS

(76) Inventor: Thomas J. Magnani, 382 North St., Greenwich, CT (US) 06830

(*) Notice: Subject to any disclaimer, the term of this patent is extended or adjusted under 35 U.S.C. 154(b) by 0 days.

(21) Appl. No.: 10/123,938

(22) Filed: Apr. 15, 2002

(65) Prior Publication Data

US 2002/0132208 A1 Sep. 19, 2002

Related U.S. Application Data

(63) Continuation of application No. 09/658,841, filed on Sep. 8, 2000, now abandoned.

(51) Int. Cl.$^7$ .............................................. A61C 17/00
(52) U.S. Cl. ........................................... 433/80; 604/20
(58) Field of Search ............................. 433/80, 89, 215, 433/216, 32; 132/311; 604/20; 15/167.1

(56) References Cited

U.S. PATENT DOCUMENTS

| | | | |
|---|---|---|---|
| 3,163,166 A | * 12/1964 | Brant et al. | 604/20 |
| 3,645,260 A | * 2/1972 | Cinotti et al. | 604/20 |
| 3,716,054 A | * 2/1973 | Porter et al. | 604/20 |
| 3,831,598 A | * 8/1974 | Tice | 604/20 |
| 4,691,718 A | * 9/1987 | Sakuma et al. | 433/32 |
| 4,969,868 A | * 11/1990 | Wang | 604/20 |
| 5,503,553 A | * 4/1996 | Hines | 433/80 |
| 5,885,711 A | * 3/1999 | Clarisse et al. | 428/407 |

OTHER PUBLICATIONS

Collins, Edwin M., D.D.S., "Desensitization of Hypersensitive Teeth," *Dental Digest*, vol. 68, No. 7 at 360–363 (Jul., 1962).

Scott, Harold M. Jr., D.D.S., "Reduction of Sensitivity by Electrophoresis," *Journal of Dentistry for Children*, vol. XXIX, No. 4 at 225–241 (Fourth Quarter, 1962).

Jensen, Arthur L., D.D.S., "Hypersensitivity controlled by iontophoresis: double blind clinical investigation," *The Journal of the American Dental Association*, vol. 68, No. 2 at 216–225 (Feb., 1964).

Schaeffer, Max L. et al., "The Effectiveness of Iontophoresis in Reducing Cervical Hypersensitivity," *Journal of Periodontology*, vol. 42, No. 11 at 695–700 (Nov., 1971).

Brännström, M. et al., "The Hydrodynamics of the Dental Tubule and of Pulp Fluid," *Caries Research*, vol. 1, No. 4 at 310–317 (1967).

Souder, Wilmer, Ph.D. et al., "Experimental Remineralization of Dentin," *The Journal of the American Dental Association*, vol. 31, No. 23 at 1579–1586 (Dec. 1, 1944).

Gangarosa, L.P. et al., "Practical considerations in iontophoresis of fluoride for desensitizing dentin," *The Journal of Prosthetic Dentistry*, vol. 39, No. 1 at 173–178 (Jan., 1978).

Cooley, Robert L. et al., "Effectiveness of potassium oxalate treatment on dentin hypersensitivity," *General Dentistry*, vol. 37, No. 4 at 330–333 (Jul.–Aug., 1989).

Ota, Norio et al., "Effect of Iontophoretic Toothbrush on Cervical Hypersensitvity," __, vol. 5 at 191–199 (1979).

"Dyna–Dental Has Something For You To Smile About" (visited and Printed Feb. 2, 2000) <http://www.ionicbrush.com>.

(List continued on next page.)

*Primary Examiner*—Kevin Shaver
*Assistant Examiner*—Melba Bumgarner
(74) *Attorney, Agent, or Firm*—Fish & Neave; Jeffrey I. Ingerman; Edward M. Arons

(57) ABSTRACT

Iontophoretic devices for treating dentin hypersensitivity are provided. One device includes a housing, an electric current source, and a replaceable cartridge mounted to or in the housing. The cartridge includes (1) a container containing an iontophoretic solution and (2) an applicator assembly fixed to the container. The assembly has a tip portion that is in electrical and fluid communication with the solution. Also provided is an iontophoretic toothbrush that includes an applicator assembly that has a brush with improved bristles.

11 Claims, 6 Drawing Sheets

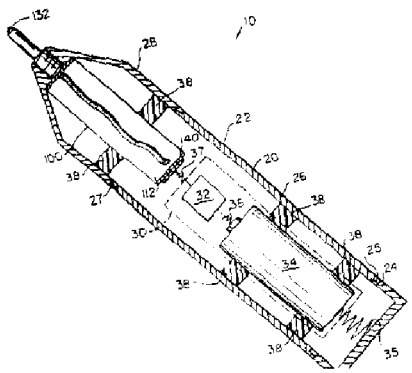

UNITED STATES PATENT AND TRADEMARK OFFICE
CERTIFICATE OF CORRECTION

PATENT NO.    : 6,743,015 B2
DATED         : June 1, 2004
INVENTOR(S)   : Thomas J. Magnani It is certified that error appears in the above-identified patent and that said Letters Patent is hereby corrected as shown below:

Title page should be deleted and substitute therefor the attached title page.

Drawings consisting of FIGS. 1-8 should be deleted to appear as per the attached sheets.

Title page,
Item [56], References Cited, OTHER PUBLICATIONS,
"Ota, Norio et al.," reference, "Hypersensitvity" should be -- Hypersensitivity --.
"Gendusa, Nelson J., D.D.S.," reference, "Special" should be -- "Special --; "Seconds" should be -- Seconds" --.

Column 1,
Line 8, "abandonded" should be -- abandoned --.
Line 31, "Brannstron" should be -- Brannstron, --.
Line 48, "Souder" should be -- Souder, --.

Column 4,
Line 7, after "to", should be inserted -- the --.

Column 5,
Line 32, "cartridge 110" should be -- cartridge 100 --.
Line 34, "to" should be deleted.
Line 58, "cartridge 110" should be -- cartridge 100 --.

Column 6,
Line 18, "114, In" should be -- 114. In --.

Column 7,
Line 22, "describe" should be -- described --.

UNITED STATES PATENT AND TRADEMARK OFFICE
CERTIFICATE OF CORRECTION

PATENT NO. : 6,743,015 B2
DATED : June 1, 2004
INVENTOR(S) : Thomas J. Magnani

It is certified that error appears in the above-identified patent and that said Letters Patent is hereby corrected as shown below:

<u>Column 8,</u>
Line 21, "within" should be -- wherein --.
Lines 34, 36, 39 and 45, "2" should be -- 7 --.

This certificate supersedes Certificate of Correction issued March 22, 2005.

Signed and Sealed this

Twenty-sixth Day of July, 2005

JON W. DUDAS
*Director of the United States Patent and Trademark Office*

(12) United States Patent
Magnani

(10) Patent No.: US 6,743,015 B2
(45) Date of Patent: Jun. 1, 2004

(54) IONTOPHORETIC APPARATUS

(76) Inventor: Thomas J. Magnani, 382 North St., Greenwich, CT (US) 06830

(*) Notice: Subject to any disclaimer, the term of this patent is extended or adjusted under 35 U.S.C. 154(b) by 0 days.

(21) Appl. No.: 10/123,938

(22) Filed: Apr. 15, 2002

(65) Prior Publication Data
US 2002/0132208 A1 Sep. 19, 2002

Related U.S. Application Data

(63) Continuation of application No. 09/658,841, filed on Sep. 8, 2000, now abandoned.

(51) Int. Cl.$^7$ ............................................. A61C 17/00
(52) U.S. Cl. ................................... 433/80; 604/20
(58) Field of Search ......................... 433/80, 89, 215, 433/216, 32; 132/311; 604/20; 15/167.1

(56) References Cited

U.S. PATENT DOCUMENTS

| | | | |
|---|---|---|---|
| 3,163,166 A | * 12/1964 | Brant et al. | 604/20 |
| 3,645,260 A | * 2/1972 | Cinotti et al. | 604/20 |
| 3,716,054 A | * 2/1973 | Porter et al. | 604/20 |
| 3,831,598 A | * 8/1974 | Tice | 604/20 |
| 4,691,718 A | * 9/1987 | Sakuma et al. | 433/32 |
| 4,969,868 A | * 11/1990 | Wang | 604/20 |
| 5,503,553 A | * 4/1996 | Hines | 433/80 |
| 5,885,711 A | * 3/1999 | Clarisse et al. | 428/407 |

OTHER PUBLICATIONS

Collins, Edwin M., D.D.S., "Desensitization of Hypersensitive Teeth," *Dental Digest*, vol. 68, No. 7 at 360–363 (Jul., 1962).

Scott, Harold M. Jr., D.D.S., "Reduction of Sensitivity by Electrophoresis," *Journal of Dentistry for Children*, vol. XXIX, No. 4 at 225–241 (Fourth Quarter, 1962).

Jensen, Arthur L., D.D.S., "Hypersensitivity controlled by iontophoresis: double blind clinical investigation," *The Journal of the American Dental Association*, vol. 68, No. 2 at 216–225 (Feb., 1964).

Schaeffer, Max L. et al., "The Effectiveness of Iontophoresis in Reducing Cervical Hypersensitivity," *Journal of Periodontology*, vol. 42, No. 11 at 695–700 (Nov., 1971).

Brännström, M. et al., "The Hydrodynamics of the Dental Tubule and of Pulp Fluid," *Caries Research*, vol. 1, No. 4 at 310–317 (1967).

Souder, Wilmer, Ph.D. et al., "Experimental Remineralization of Dentin," *The Journal of the American Dental Association*, vol. 31, No. 23 at 1579–1586 (Dec. 1, 1944).

Gangarosa, L.P. et al., "Practical considerations in iontophoresis of fluoride for desensitizing dentin," *The Journal of Prosthetic Dentistry*, vol. 39, No. 1 at 173–178 (Jan., 1978).

Cooley, Robert L. et al., "Effectiveness of potassium oxalate treatment on dentin hypersensitivity," *General Dentistry*, vol. 37, No. 4 at 330–333 (Jul.–Aug., 1989).

Ota, Norio et al., "Effect of Iontophoretic Toothbrush on Cervical Hypersensitvity," __, vol. 5 at 191–199 (1979).

"Dyna–Dental Has Something For You To Smile About" (visited and Printed Feb. 2, 2000) <http://www.ionicbrush.com>.

(List continued on next page.)

*Primary Examiner*—Kevin Shaver
*Assistant Examiner*—Melba Bumgarner
(74) *Attorney, Agent, or Firm*—Fish & Neave; Jeffrey I. Ingerman; Edward M. Arons

(57) ABSTRACT

Iontophoretic devices for treating dentin hypersensitivity are provided. One device includes a housing, an electric current source, and a replaceable cartridge mounted to or in the housing. The cartridge includes (1) a container containing an iontophoretic solution and (2) an applicator assembly fixed to the container. The assembly has a tip portion that is in electrical and fluid communication with the solution. Also provided is an iontophoretic toothbrush that includes an applicator assembly that has a brush with improved bristles.

11 Claims, 6 Drawing Sheets